US011219559B2

(12) United States Patent
Atkins et al.

(10) Patent No.: US 11,219,559 B2
(45) Date of Patent: Jan. 11, 2022

(54) NASAL DRIP PAD

(71) Applicant: ENT Solutions Group, LLC, San Antonio, TX (US)

(72) Inventors: Lori Jean Atkins, San Antonio, TX (US); James H. Atkins, Jr., San Antonio, TX (US)

(73) Assignee: ENT SOLUTIONS GROUP, LLC, San Antonio, TX (US)

( * ) Notice: Subject to any disclaimer, the term of this patent is extended or adjusted under 35 U.S.C. 154(b) by 625 days.

(21) Appl. No.: 15/092,783

(22) Filed: Apr. 7, 2016

(65) Prior Publication Data

US 2016/0296383 A1 Oct. 13, 2016

Related U.S. Application Data

(60) Provisional application No. 62/144,011, filed on Apr. 7, 2015.

(51) Int. Cl.
| *A61F 13/42* | (2006.01) |
| *A61F 13/12* | (2006.01) |
| *A61F 13/58* | (2006.01) |

(52) U.S. Cl.
CPC ............ *A61F 13/42* (2013.01); *A61F 13/126* (2013.01); *A61F 13/58* (2013.01)

(58) Field of Classification Search
CPC ........ A61F 13/42; A61F 13/58; A61F 13/126; A61F 13/00055; A61F 13/00059; A61F 13/00029; A61F 13/00042
See application file for complete search history.

(56) References Cited

U.S. PATENT DOCUMENTS

| 2,087,042 | A | * | 7/1937 | Phillips | A61F 5/56 128/206.18 |
| 2,161,607 | A | * | 6/1939 | Anderson | A62B 23/06 128/206.18 |
| 2,361,506 | A | * | 10/1944 | Gray Smith | A61F 15/002 602/58 |
| 3,654,929 | A | * | 4/1972 | Nilsson | A61F 13/15211 604/364 |
| 3,805,790 | A | * | 4/1974 | Kaczmarzyk | A61F 13/47245 604/369 |
| 4,774,935 | A | * | 10/1988 | Aronsohn | A61F 5/30 128/97.1 |
| 5,007,114 | A | * | 4/1991 | Numano | A61M 16/06 128/201.13 |
| 5,284,469 | A | * | 2/1994 | Jasen | A61F 13/126 128/858 |

(Continued)

FOREIGN PATENT DOCUMENTS

| CA | 2809834 A1 * | 3/2012 | ........... A62B 23/025 |
| GB | 2200553 A * | 8/1988 | ........... A61F 13/126 |

*Primary Examiner* — Catharine L Anderson
*Assistant Examiner* — Arjuna P Chatrathi
(74) *Attorney, Agent, or Firm* — Campbell Stephenson LLP

(57) ABSTRACT

An apparatus that includes an absorber, a positioner, and an estimator, where the positioner and estimator are coupled to the absorber. The absorber includes absorbent material configured to capture nasal drainage. The positioner places the absorber in proximity to a person's nose. The estimator provides an indication of an amount of drainage captured by the absorber.

24 Claims, 9 Drawing Sheets

(56) References Cited

U.S. PATENT DOCUMENTS

| | | | | |
|---|---|---|---|---|
| 5,312,324 | A | * | 5/1994 | Walthour .............. A61F 13/126 |
| | | | | 128/206.18 |
| 5,362,303 | A | | 11/1994 | Jasen et al. ..................... 602/17 |
| 5,383,891 | A | * | 1/1995 | Walker .............. A61F 13/00063 |
| | | | | 206/438 |
| 5,622,059 | A | * | 4/1997 | McClellan .............. F25D 11/00 |
| | | | | 312/116 |
| 5,727,544 | A | * | 3/1998 | Miura .................... A41D 13/11 |
| | | | | 128/201.13 |
| 6,185,740 | B1 | * | 2/2001 | Zegarelli ................ A61C 3/025 |
| | | | | 2/9 |
| 6,517,509 | B1 | | 2/2003 | Shippert ......................... 604/11 |
| 6,532,598 | B1 | * | 3/2003 | Cardarelli .............. A41D 13/11 |
| | | | | 128/206.19 |
| 2002/0062114 | A1 | * | 5/2002 | Murai ..................... G01N 5/02 |
| | | | | 604/385.01 |
| 2006/0114754 | A1 | * | 6/2006 | MacDonald ............ A61F 13/42 |
| | | | | 368/327 |
| 2007/0023046 | A1 | * | 2/2007 | Huang ............... A41D 13/1161 |
| | | | | 128/206.12 |
| 2010/0159599 | A1 | * | 6/2010 | Song ....................... A61F 13/42 |
| | | | | 436/39 |
| 2011/0218509 | A1 | * | 9/2011 | Dontas .................... A61F 13/10 |
| | | | | 604/365 |
| 2014/0336557 | A1 | * | 11/2014 | Durdag .................. A61L 15/26 |
| | | | | 602/48 |
| 2016/0008179 | A1 | | 1/2016 | Hart .............................. 604/377 |

\* cited by examiner

NASAL DRIP PAD

RELATED APPLICATIONS

This application claims the domestic benefit under Title 35 of the United States Code §119(e) of U.S. Provisional Patent Application Ser. No. 62/144,011, entitled "Nasal Drip Pad," filed Apr. 7, 2015, which is hereby incorporated by reference in its entirety and for all purposes as if completely and fully set forth herein.

FIELD OF THE INVENTION

This invention relates to medical instruments, in particular to those used to treat sinus conditions.

DESCRIPTION OF THE RELATED ART

Following various nasal procedures, patients often experience drainage from the nose, including nasal bleeding and/or other nasal discharge. A nasal dressing or bandage can be used to capture the drainage. Issues such as occlusion of the nasal passages, crusting, adhesion, and other issues can cause the use of nasal dressings to be uncomfortable and unsightly. Furthermore, patients may not know how often to change such nasal dressings, which can contribute to odor, bacterial growth, and failure to detect issues that should be brought to the attention of a medical professional.

Another challenge faced by medical professionals in such situations is the lack of a mechanism for estimating the volume of blood/fluid lost by a patient after the patient has left the location where the procedure was performed. Subsequently, if a patient calls and complains of blood loss or other such issues after a procedure, the medical professional is forced to rely on the patient's "layman's description" of the issue at hand, as supplemented by information regarding patient history and physical examination for decision-making. Depending on the amount and nature of drainage a patient experiences, measures such as blood work and visits to the office or emergency room may be initiated. Unfortunately, the patient's characterization of such issues operating system often inaccurate, exaggerated, imprecise, or otherwise unreliable, leading to unnecessary follow-up office visits, and the like.

BRIEF DESCRIPTION OF THE DRAWINGS

The present invention may be better understood, and its numerous objects, features, and advantages made apparent to those skilled in the art, by referencing the accompanying drawings.

Figure 1:
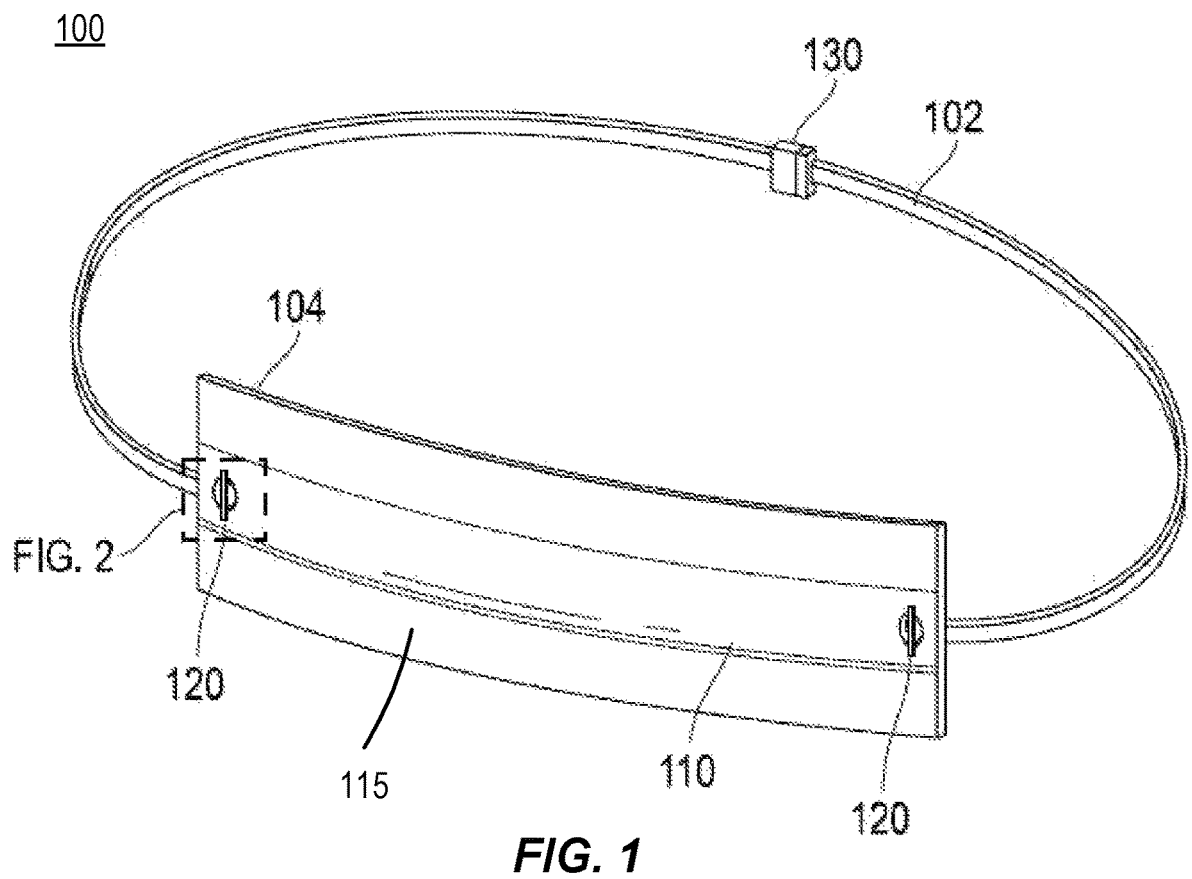
FIG. 1 illustrates aspects of a nasal drip pad, according to one embodiment.

While the invention is susceptible to various modifications and alternative forms, specific embodiments of the invention are provided as examples in the drawings and detailed description. It should be understood that the drawings and detailed description are not intended to limit the invention to the particular form disclosed. Instead, the intention is to cover all modifications, equivalents and alternatives falling within the spirit and scope of the invention as defined by the appended claims.

DETAILED DESCRIPTION

The present disclosure relates to a nasal drip pad and a method of using a nasal drip pad. The nasal drip pad includes an absorber. In one embodiment, the absorber includes absorbent material. The absorbent material is configured to absorb drainage, such as nasal drainage from a person's nose. The nasal drip pad also includes a positioner. The positioner is coupled to the absorber and includes a mechanism for securing the nasal drip pad to a person's head. In one embodiment, the positioner includes one or more straps configured to position the absorber in proximity to the person's nostrils. In one embodiment, the nasal drip pad also includes an estimator. The estimator is configured to indicate an amount of drainage or fluid loss. In one embodiment, the estimator includes one or more gradations, or any other suitable indicators. The present description also relates to one or more methods of configuring and using the nasal drip pad by patients and/or medical professionals.

A number of scenarios exist in which a person can experience drainage from the nose. For example, after a medical procedure affecting the sinuses, patients commonly experience drainage of blood and/or mucus from the nose. Such drainage can continue, in some cases, for a number of days. Absorbent material, such as a bandage and/or dressing can be positioned in proximity to the nose to capture such drainage. Issues related to patient safety and comfort exist that suggest care in selecting the type of dressing to be used. For example, patient's facial tissues are often quite sensitive after nasal surgery. Therefore, any dressing should be positioned loosely enough to avoid causing the patient undue discomfort. However, if the dressing is not positioned securely, the dressing may not capture all of the drainage. Furthermore, the amount of drainage can vary based upon the person, the person's physical anatomy, the type of procedure, and other such factors. The fact that it is difficult to predict exactly how much drainage will be experienced complicates the process of effectively informing the person what to expect. For example, patients should be informed of what is normal in terms of amount of drainage, how often the dressing should be changed, and whether to seek medical advice or assistance in the hours and days following a procedure. However, a given patient's perception of the patient's expected situation varies widely, and complicates proper management of such situation by the patient, the physician, and he physician's office personnel.

Described herein is a nasal drip pad that is well adapted to increase patient comfort and safety, reduce after-calls, provide patients with objective information regarding normal amounts of drainage, allow the patient to provide measureable data to medical professional by phone, as well as numerous other benefits and advantages. The nasal drip pad is described with regard to the attached figures, in which like numerals refer to like components throughout the figures. While the present description refers to positioning a nasal drip pad in proximity to a person's face, it is understood that the described embodiments can be used in other contexts, such as other types of medical procedures involving other parts of the body.

FIG. 1 is a diagram showing a front view of nasal drip pad 100, according to one embodiment. In one embodiment, nasal drip pad 100 includes a positioner 102, referred to herein as a positioning element, and an absorber 104, referred to herein as an absorbent element. As described below, in some embodiments these elements includes a number of additional components.

In the example shown in FIG. 1, positioning element 102 is implemented as a strap that can be placed around a patient's head to secure absorbent element 104 to the patient's face. Positioning element 102 can be implemented using a band comprising elastic, nylon, cotton, or any other suitable material.

The length of positioning element 102 can be changed via an adjuster 130. Shortening the length of positioning element 102 has the effect bringing absorbent element 104 closer to the person's face, e.g., increasing the tightness. Adjusting the tightness of positioning element 102 permits adjustment of the security of nasal drip pad 100 and, when tightened, reduces the likelihood of nasal drip pad slipping off and of drainage escaping. Decreasing the tightness of positioning element 102 tends to reduce the proximity of absorbent element 104 to the person's face. This tends to increase the airflow around the person's nose and mouth, providing additional comfort. Adjusting the length of positioning element 102 also tends to change the shape of absorbent element 104 that contacts the person's skin. Tightening positioning element 102 tends to increase the surface area of contact between absorbent element 104 and the person's skin, while loosening positioning element 102 tends to decrease the surface area of contact absorbent element 104 and the person's skin. Adjusting the amount of contact may be performed based on the type of material used in absorbent element 104. For example, material that is more absorbent can operate more effectively with less surface area in contact with a person's skin than can material that is less absorbent. Adjuster 130 can be used to accommodate different size heads, as well as different preferences for tightness.

As shown, positioning element 102 is attached to absorbent element via fasteners 120. Fasteners 120 can be implemented using hooks, clips, adhesives, Velcro®, magnets, or any other mechanism that allows positioning element 102 to be detached from absorbent element 104. In one embodiment, positioning element 102 and absorbent element 104 are permanently attached, for example, sewn, adhered, stapled, or manufactured as a single component. While one point of connection is shown on a proximal end of absorbent element 104 and one point of connection is shown on a distal end of absorbent element 104, more points of connection can be used. For example, positioning element 102 can be fastened to absorbent element 104 by two or more points of connection on each side, and/or points of connection along the upper or lower edges. Additional points of connection can impact sealing or fit properties of nasal drip pad 100.

Absorbent element 104 includes an exterior surface 115, also referred to as a non-absorbent shield. When nasal drip pad 100 is in use, exterior surface 115 is directed away from the patient's face. In one embodiment, exterior surface 115 is implemented using an opaque, non-absorbent material. Exterior surface 115 prevents excess drainage from escaping the nasal drip pad. For example, if absorbent material included in absorbent element 104 becomes saturated, any additional drainage can be prevented from spilling out of nasal drip pad 100 by exterior surface 115. Exterior surface 115 also shields unsightly absorbent material from view. In one embodiment, exterior surface 115 is implemented using absorbent material and provides additional capacity to absorb drainage. Exterior surface 115 forms, in on embodiment, a substrate to which one or more absorbers and/or estimators can be coupled, e.g., using adhesives, clips, and/or any other type of fastener, either removably or permanently.

Nasal drip pad 100 includes, optionally, one or more formable members 110. Formable members 110 can be manually manipulated to change the shape of nasal drip pad 100. Such a formable member can be fabricated from, for example, wire, tubing, or any other material that is readily bendable and holds its shape once having been bent. Bending formable member 110 into different shapes allows the fit of nasal drop pad 100 to be altered depending on the shape of a patient's face, comfort, and other such considerations. As human faces are generally curved, formable member can be used to cause nasal drip pad 100 to more closely conform to the curves of a person's face.

Figure 2:
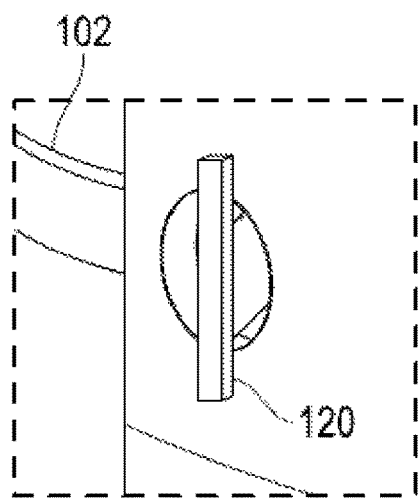
FIG. 2 illustrates a blowup view of aspects of a nasal drip pad, according to one embodiment.

FIG. 2 illustrates a blow up view of one of fasteners 120. As shown, the fastener includes a bar and a ring. The length of the bar is greater than the diameter of the ring. In operation, the bar is positioned parallel to positioning element 102 and passed through the ring, traversing from the posterior side of absorbent element 104 to the anterior side of absorbent element 104, or vice versa. The bar is then released, and positioned perpendicular to positioning element 102, whereupon the bar no longer fits through the ring. The embodiment shown in FIG. 2 shows one example of coupling positioning element 102 to absorbent element 104, though any suitable mechanism for mechanically coupling positioning element 102 and absorbent element 104 can be used.

Figure 3A:
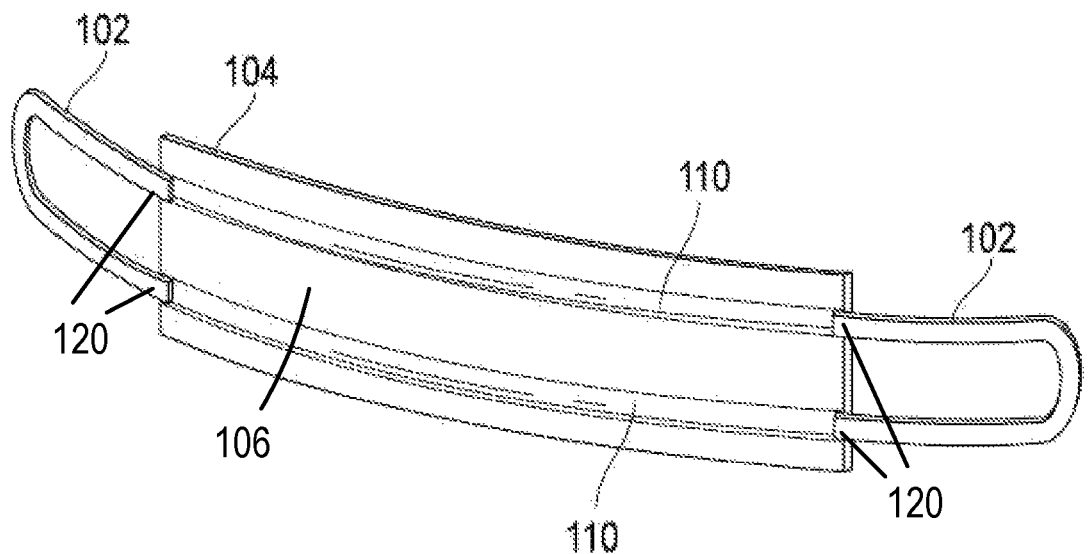
FIG. 3A illustrates aspects of a nasal drip pad, according to one embodiment.

FIG. 3A shows an embodiment of nasal drip pad 100 in which positioning element 102 is implemented as a pair of looped straps. The looped straps can be placed around a patient's ears to secure absorbent element 104 to the patient's face. Though not shown, the looped straps include, in one embodiment, adjustors that can be used to change the length of the looped straps, thereby adjusting the seal and tightness of nasal drip pad 100 to the wearer's face. Nasal drip pad 100 includes, optionally, one or more formable members 110. Formable members 110 can be manually manipulated to change the shape of nasal drip pad 100. Doing so allows the fit of nasal drop pad 100 to be altered depending on the shape of a patient's face, comfort, and other such considerations. Nasal drip pad 100 also includes a front surface 106. Absorbent element 104 is secured to positioning element 102 via fasteners 120. As shown in FIG. 3A, fasteners 120 attach positioning element 102 to absorbent element 104 in two places in proximity to each of a proximal end and distal end of absorbent element 104. That is, fasteners 120 secure absorbent element 104 to positioning element 102 at an upper location and a lower location on each end. Though FIG. 3A illustrates positioning element 102 as including two straps, more or fewer straps can be used to provide a mechanism to secure nasal drip pad 100 to a person's face.

Figure 3B:
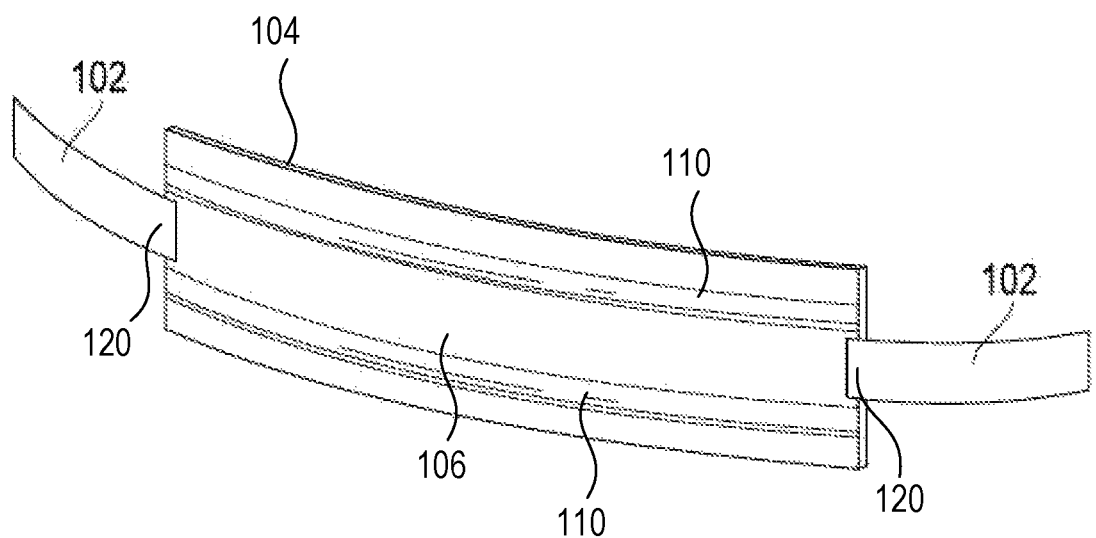
FIG. 3B illustrates aspects of a nasal drip pad, according to one embodiment.

FIG. 3B shows an embodiment of nasal drip pad 100 in which positioning element 102 is implemented using adhesives. As shown in FIG. 3B, adhesive strips are affixed to a first and second end of nasal drip pad 100 at attachment point 120. The adhesive strips can be attached to absorbent element by virtue of the adhesive properties of the strips themselves, or by some other means, such as staples or any other mechanical coupling mechanism. The adhesive strips can adhere directly to a patient's skin. In one embodiment, adhesive material can be incorporated or attached to absorbent element 104 facing the patient's face. The adhesive material can be included along one or more edges of absorbent element 104. When incorporated along the bottom edge of absorbent element 104, the adhesive provides additional security against leaks.

Figure 4:
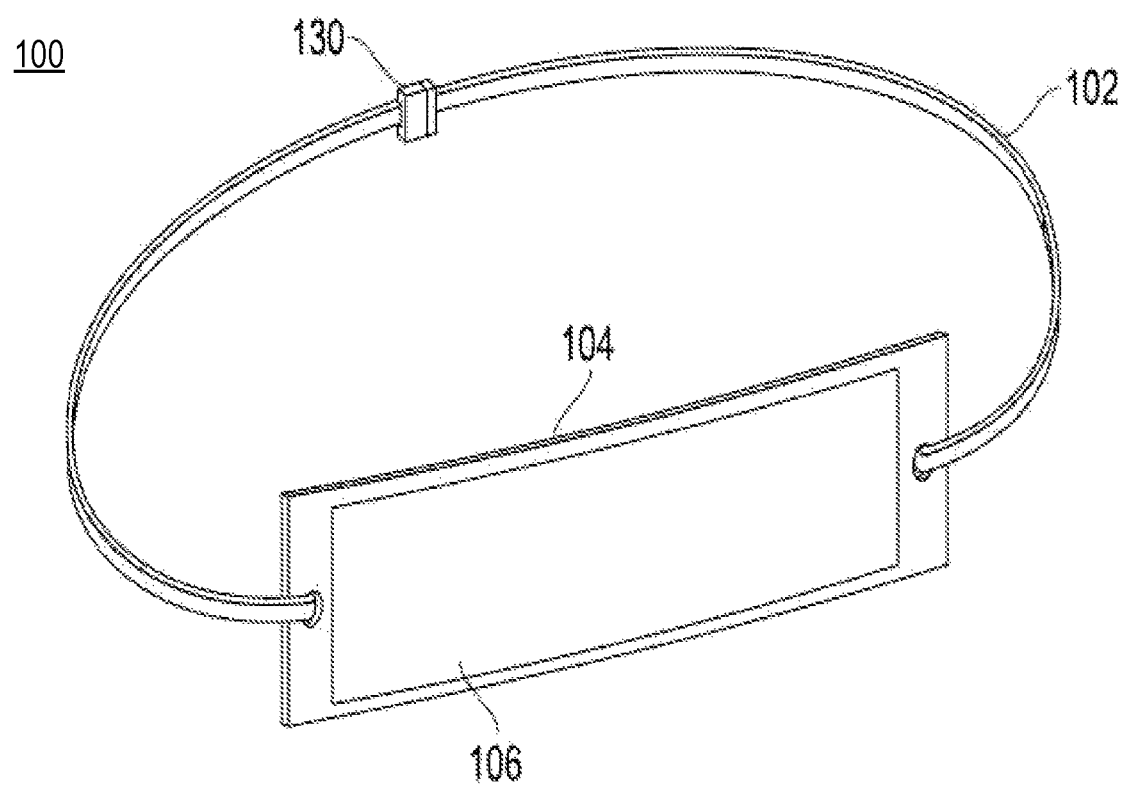
FIG. 4 illustrates aspects of a nasal drip pad, according to one embodiment.

FIG. 4 shows a back view of nasal drip pad 100. Nasal drip pad 100 includes one or more positioning elements 102 having adjustor 130 and absorbent element 104. Absorbent element 104 includes absorbent material 106. The size, amount, and type of absorbent material included in absorbent element 104 can vary. Nasal drip pad 100 is configured such that when nasal drip pad 100 is in use, absorbent material 106 is positioned towards the patient's face, either in contact with the patient's face or close to the patient's face. Absorbent material 106 can be implemented using sterile gauze, or any other absorbent material, such as, for example, a mesh of silk, linen, or cotton. Various types of materials having varying known rates of absorption can be used, and can be selected based on the expected amount and viscosity of the discharge. Absorbent material 106 can also be configured to wick moisture away from the skin of the person wearing nasal drip pad 100, e.g., via the inclusion of a nylon component in absorbent element 104. In one embodiment, absorbent element 104 includes a non-stick coating to prevent absorbent material from sticking to the person's skin. Absorbent element 104 also includes, in one embodiment, antibacterial material, such as antibacterial coating, fabric, liquid, powder, or the like.

Figure 5A:
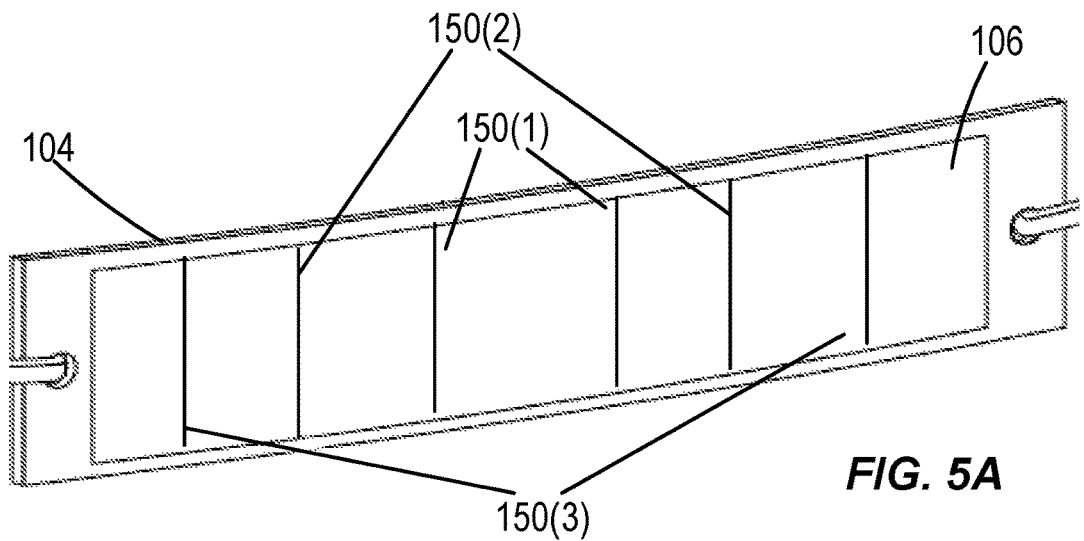
FIG. 5A illustrates aspects of a nasal drip pad, according to one embodiment.

FIG. 5A shows an example of absorbent element 106 that includes an estimation element, also referred to herein as an estimator. The estimator includes, in one embodiment, a series of gradations, or marks, 150(1)-150(3), and is referred to collectively as estimator 150. The gradations can be used to estimate an amount of material, such as fluid, that has been absorbed by absorbent element 106. For example, estimator 150 can describe an area on absorbent element 104 that, when multiplied by the thickness of absorbent element 104 and an absorbency coefficient, can provide an estimation of the amount of fluid absorbed by absorbent element 104. A rate of fluid loss can be calculated by dividing the calculated amount of fluid by a time value, such as the amount of time that the nasal drip pad has been worn or since the last calculation was made.

Estimator 150 can include more or fewer marks, defining more or fewer regions. Though shown evenly spaced, the spacing of the marks can vary based, for example, on the position of the marks on absorbent element 104 relative, e.g., to the center of absorbent element 104. The shapes of the marks can also vary depending, for example, on the type of drainage expected and the absorbent properties of absorbent element 104. In one embodiment, colors can be used to designate certain regions. For example, absorbent element 104 can include a region that is shaded green to indicate a safe level of drainage. If absorbed drainage exceeds a boundary or threshold and passes beyond the green shaded region, an unsafe level of drainage is indicated, and the person should take further measures, such as contacting a medical professional. Volume unit values, such as in 100 ml increments, are included in one embodiment. The markings can be, as shown, included on absorbent material 106 and/or can be on absorbent element 104 (e.g., around, behind, and/or above absorbent material 106). In one embodiment, absorbent element 104 can be configured with a gradient. For example, absorbent element 104 can be implemented having increasingly absorbent material in certain areas, e.g., closer to the edges of the nasal drip pad, or can vary in thickness, e.g., become progressively thicker towards an edge, thus increasing the absorbency. In embodiments having varying absorbency, the estimator values are arranged to correspond. For example, in the case where the space between two lines indicates an amount of fluid, the distance between the lines diminishes as absorbency increases. In one embodiment, estimator 150 is represented on a separate portion of material which can be attached to absorbent element 104, e.g., as an overlay.

Figure 5B:
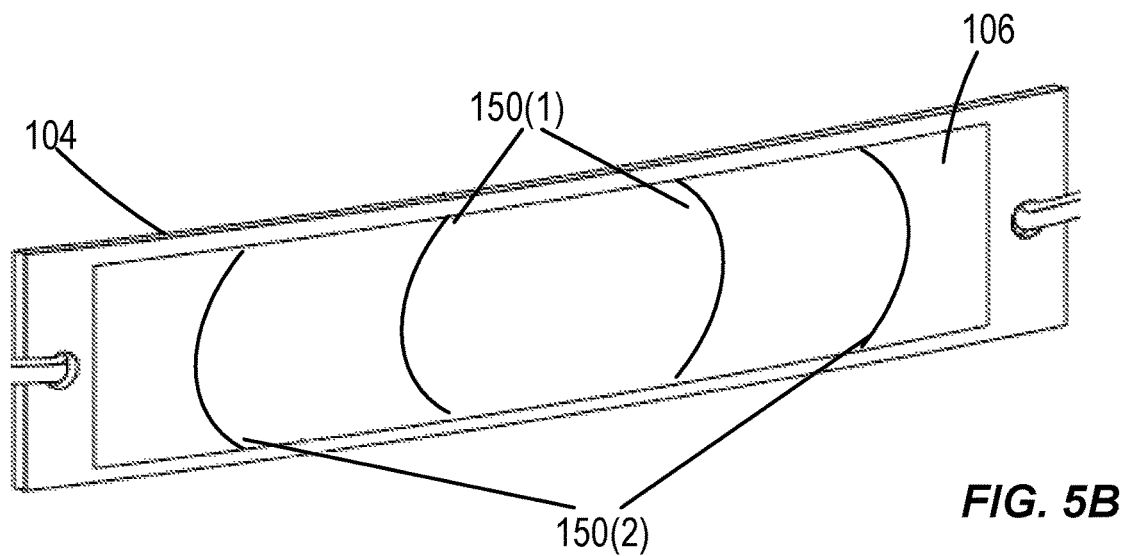
FIG. 5B illustrates aspects of a nasal drip pad, according to one embodiment.

FIG. 5B shows an example of absorbent element 106 that includes an estimation element, also referred to herein as an estimator. The estimator includes a series of gradations, or marks, 150(1)-150(2), and is referred to collectively as estimator 150. Estimator 150 can be used to estimate an amount of material, such as fluid, that has been absorbed by absorbent element 106. The estimator shown in FIG. 5B differs from that shown in FIG. 5A by virtue of having gradations of a different shape.

Figure 5C:
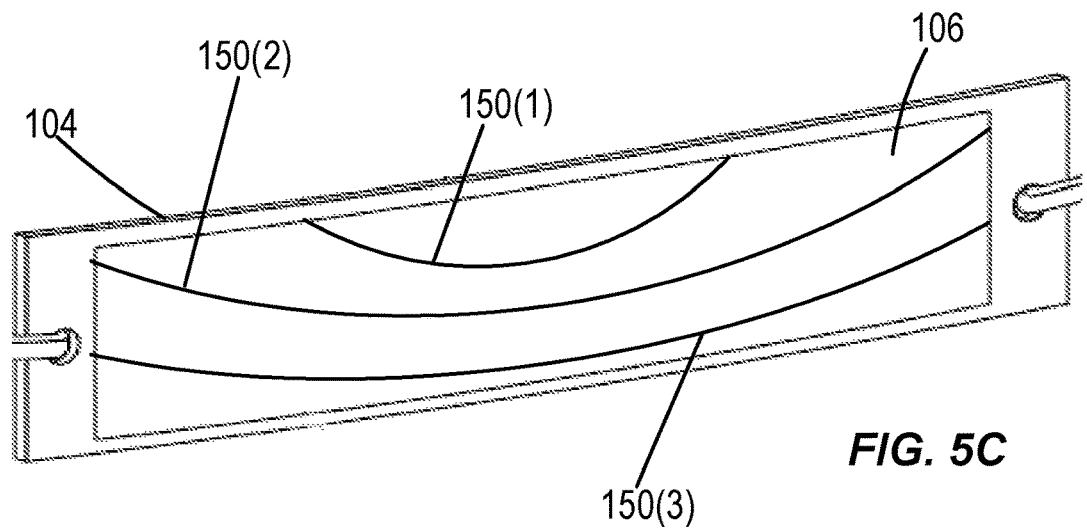
FIG. 5C illustrates aspects of a nasal drip pad, according to one embodiment.

FIG. 5C shows an example of absorbent element 106 that includes an estimation element, also referred to herein as an estimator. The estimator includes a series of gradations, or marks, 150(1)-150(3), and is referred to collectively as estimator 150. Estimator 150 can be used to estimate an amount of material, such as fluid, that has been absorbed by absorbent element 106. The estimator shown in FIG. 5C differs from that shown in FIGS. 5A and 5C by virtue of having gradations of a different shape.

Figure 6:
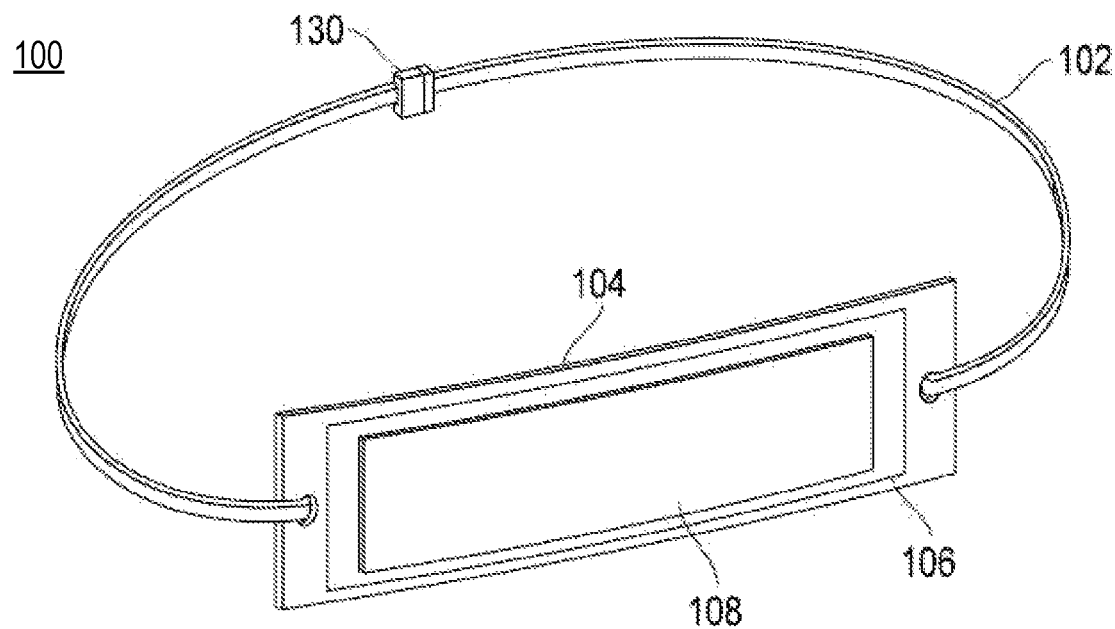
FIG. 6 illustrates aspects of a nasal drip pad, according to one embodiment.

FIG. 6 shows an example nasal drip pad 100 having multiple portions of absorbent material 106 and 108. For example, 106 shows a first type of absorbent material having a first size and 108 shows a second type of absorbent material having a second size. In one embodiment, a medical professional can select the types and sizes of absorbent material based on one or more properties of the material. For example, absorbent material 108, which is intended to contact the person's skin, can be selected due to inclusion of a non-stick coating, where absorbent material 106, which is not intended to contact the person's skin, can be selected as a less expensive material without the non-stick coating.

Figure 7:
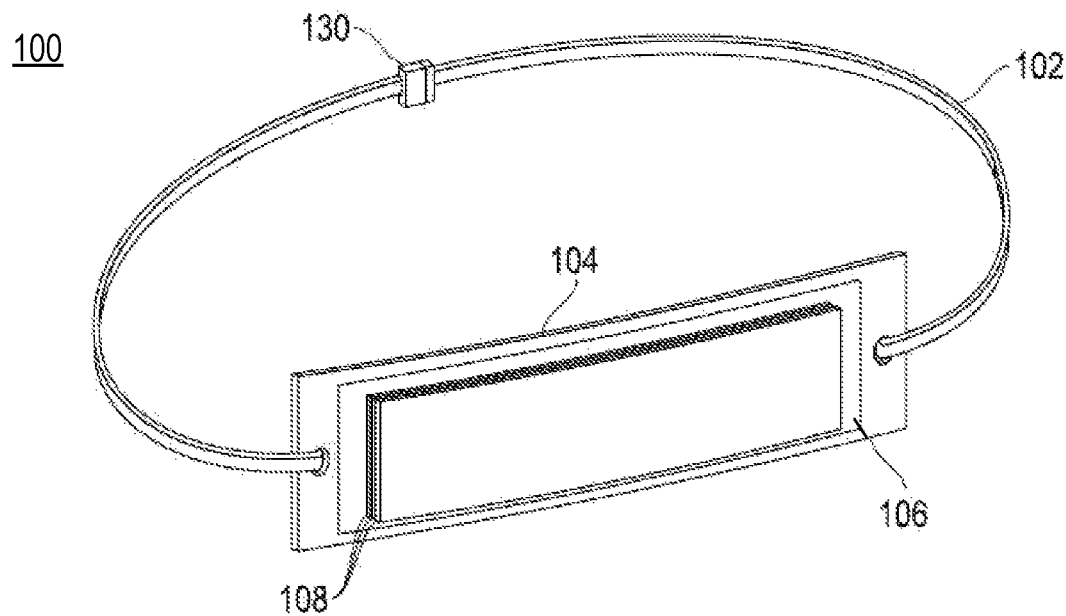
FIG. 7 illustrates aspects of a nasal drip pad, according to one embodiment.

FIG. 7 shows an example nasal drip pad 100 having multiple portions of absorbent material 106 and 108. In one embodiment, absorbent material 108 includes multiple layers, the absorption capacity of each of which is known. In this manner, the amount of drainage absorbed by nasal drip pad 100 can be estimated by determining the extent of saturation to various layers. Each layer can have the same or different absorption capacities, relative to the other layers. The multiple layers themselves form an estimator, such as estimator 150, of a configurable number of discrete layers that can be independently attached and removed, e.g., using adhesive. Based on the number of layers that have absorbed drainage, the amount of drainage can be estimated.

Figure 8:
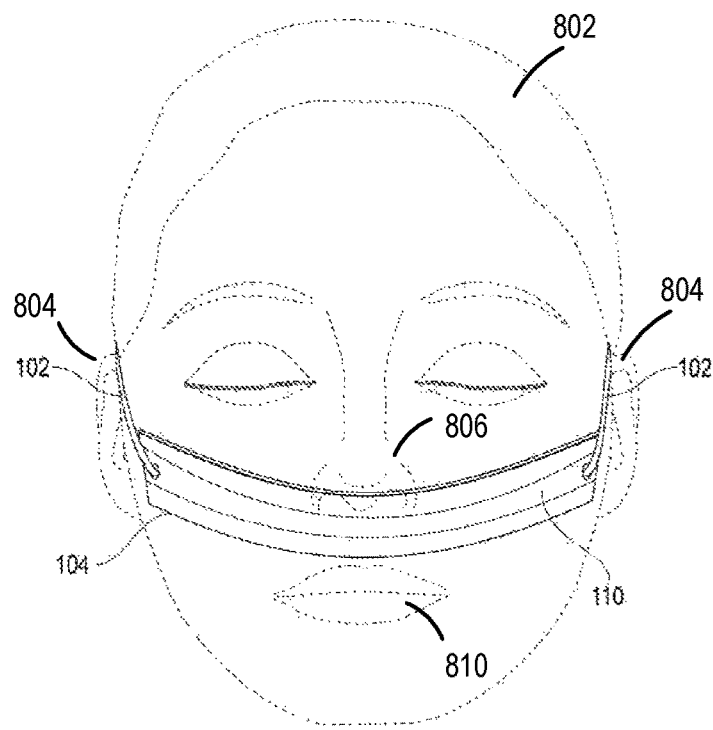
FIG. 8 illustrates a frontal view of a nasal drip pad in use, according to one embodiment.
Figure 9:
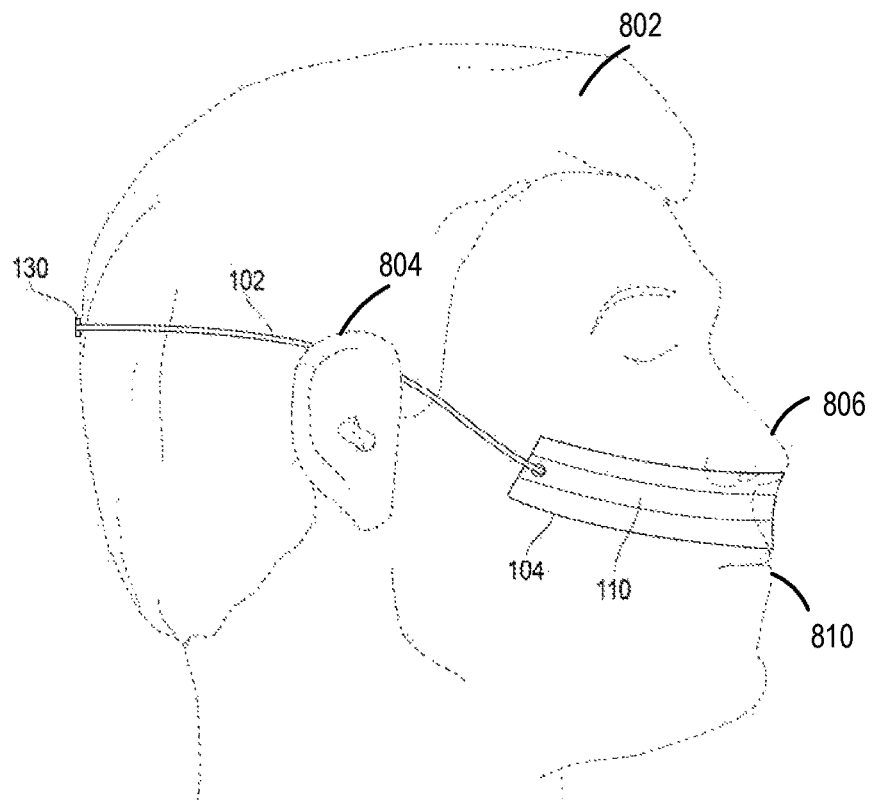
FIG. 9 illustrates a side view of a nasal drip pad in use, according to one embodiment.

FIG. 8 shows a front view of nasal drip pad 100 positioned on a person's head 802. Positioning element 102 passes over the person's ears 804 and positions absorbent element 104 below the person's nose 806 and above the person's mouth 810. FIG. 9 shows a side view of nasal drip pad 100 positioned on a person's head 802. Positioning element 102 passes over the person's ears 804 and positions absorbent element 104 below the person's nose 806 and above the person's mouth 810.

Figure 10:
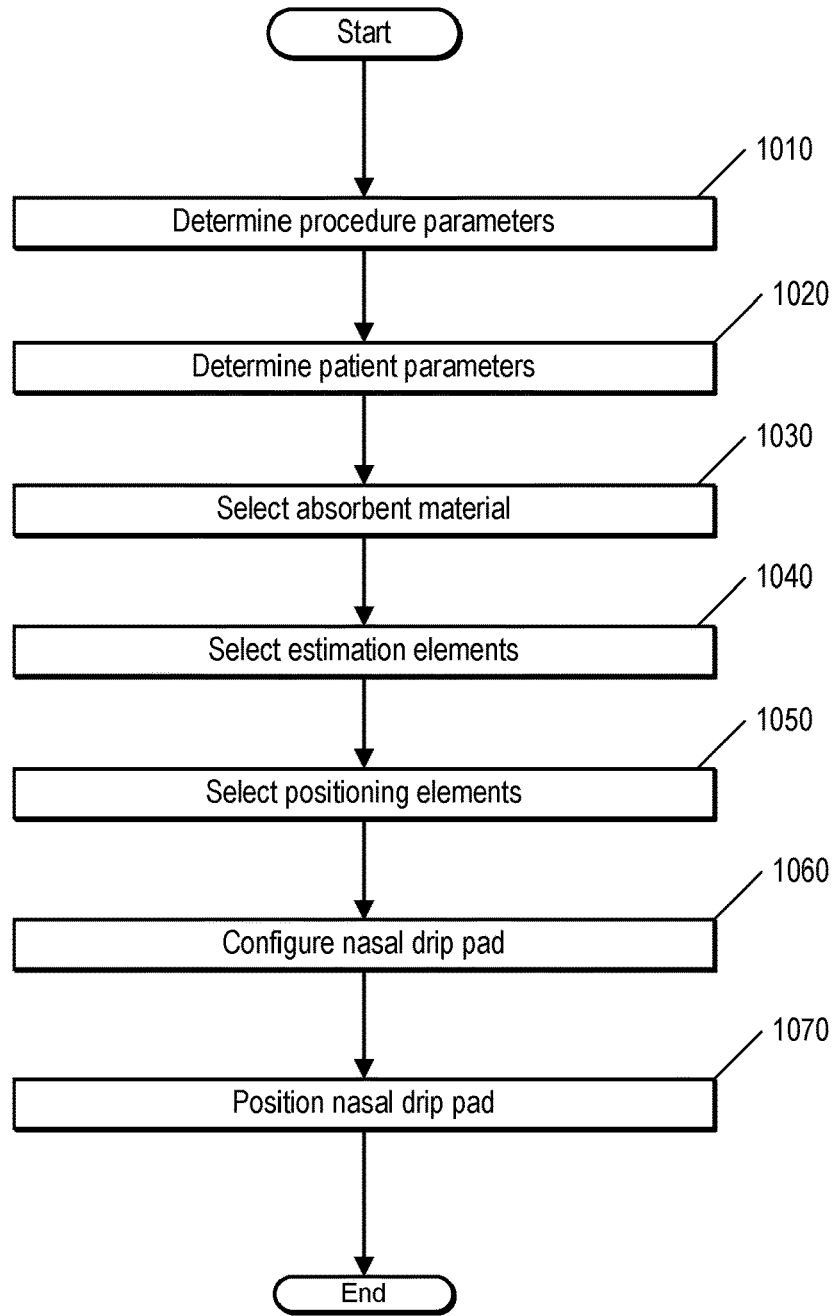
FIG. 10 is a flow diagram illustrating a method of configuring a nasal drip pad, according to one embodiment.

FIG. 10 is a flow diagram illustrating a method of employing a nasal drip pad, such as nasal drip pad 100 of FIG. 1. At 1010, a user, such as a medical professional, detects one or more parameters related to a procedure, such as sinus surgery, for which the nasal drip pad is being used. For example, the user determines a type of procedure, the scope of the procedure, expected recovery time, any potential complicating factors, and the like. Different types of nasal drip pads can be selected based on the procedure parameters. For example, the amount and type of drainage can vary based on the procedure, so a more absorbent nasal drip pad can be selected for a first type of procedure and a less absorbent nasal drip pad can be selected for a second type of procedure. The user's selection of the nasal drip pad's size and positioning elements can also be affected by procedure parameters.

The user determines, at 1020, one or more patient parameters. Patient parameters can include, for example, the size of the patient, physical structure, age, medical conditions, sensitivity, and the like. At 1030, the user selects the absorbent material to be included in the nasal drip pad. For example, the user can select different types and/or shapes of absorbent material depending on the procedure parameters and/or the patient parameters. The user selects, at 1040, the estimator to be used. The user determines shape, capacity, and implementation features for the estimator. For example, the user can determine whether closely spaced or widely spaced markings are used, whether multiple layers of absorbent material are used, whether volume measurement units are used, and the like.

The user selects, at 1050, the positioning elements to include in nasal drip pad 100. In one embodiment, this involves selecting the type and/or number of positioning element to be used. This decision can be made based on, for example, the type of procedure and the patient's predicted sensitivity following the procedure. At 1060, the user configures the nasal drip pad. In one embodiment, this involves retrieving components and assembling the components, for example, fastening one or more positioning elements to one or more absorbent element, adjusting the length of the positioning elements, assembling layers of absorbent material, affixing estimation elements, and the like. The user, at 1070, positions the nasal drip pad on the person's head and ensures proper fit.

Figure 11:
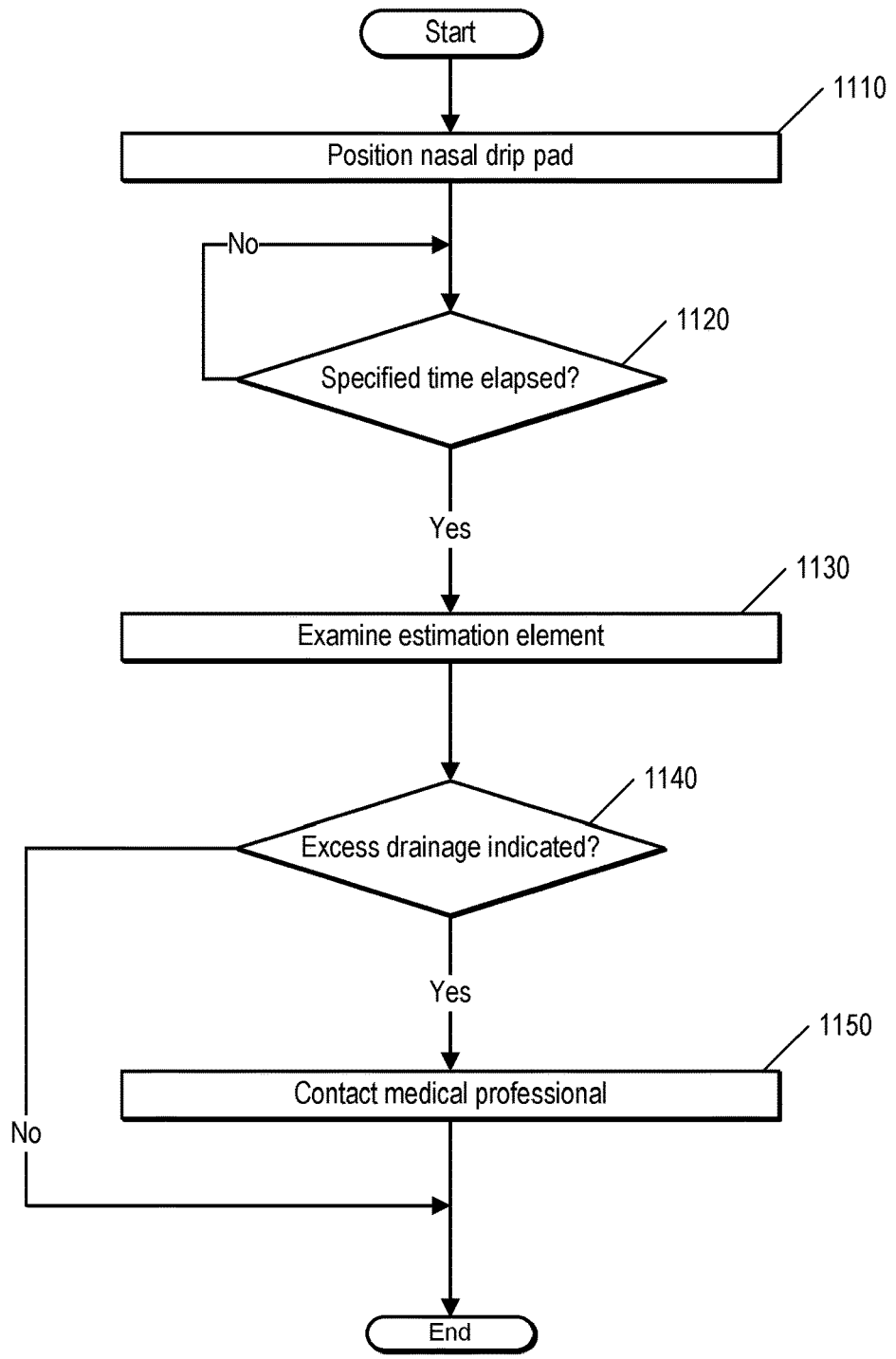
FIG. 11 is a flow diagram illustrating a method of using a nasal drip pad, according to one embodiment.

FIG. 11 is a flow diagram illustrating a method of employing a nasal drip pad, such as nasal drip pad 100 of FIG. 1. At 1110, a person, such as a patient who is, has recently, or is in expectation of imminently experiencing nasal drainage, positions the nasal drip pad over the person's head such that the positioning elements secure the nasal drip pad against the person's face above the mouth and below the nose in a position to capture and absorb the drainage. The person determines, at 1120, whether a specified time has elapsed. For example, the person consults instructions provided by a medical profession for proper use of the nasal drip pad. The instructions indicate when the nasal drip pad should be checked to determine whether excess drainage has occurred and when the nasal drip pad should be changed or replaced.

In response to determining, at 1120, that the specified amount of time has elapsed, the user examines the estimator included with the nasal drip pad. For example, the person can compare the amount of absorption, e.g., the soiled portion of the absorbent material, with one or more markings and determine whether the amount of absorption has exceeded an expected amount for the elapsed time. If so, at 1150, the person contacts a medical professional.

Figure 12:
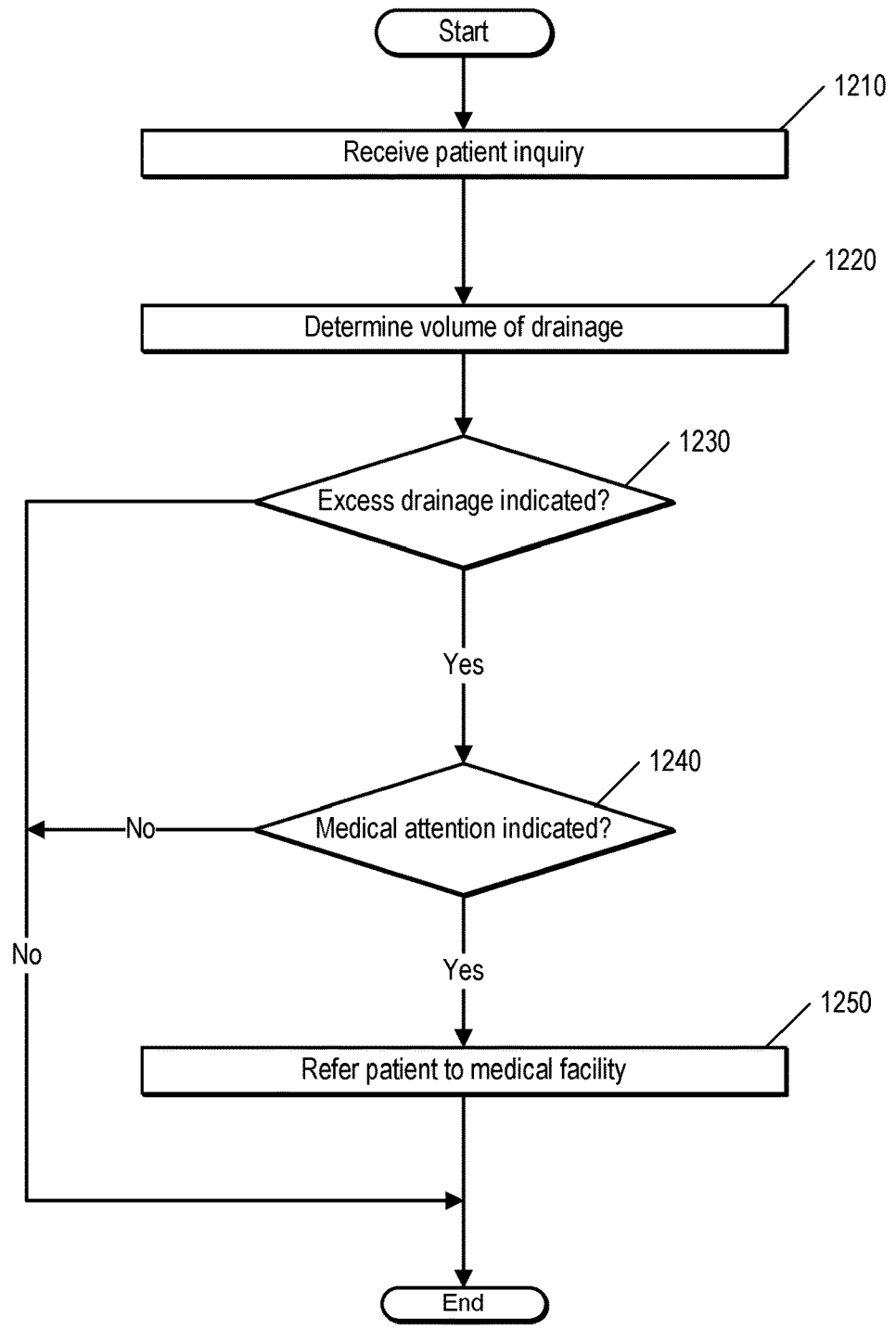
FIG. 12 is a flow diagram illustrating a method of using a nasal drip pad, according to one embodiment.

FIG. 12 is a flow diagram illustrating a method of employing a nasal drip pad, such as nasal drip pad 100 of FIG. 1, which can be performed by patients and medical personnel. In one embodiment, the nasal drip pad is or has been worn by a person, such as a patient, to absorb nasal drainage, e.g., following a medical procedure. At 1210, a user, such as a medical professional, receives a patient inquiry. The inquiry can be received via one or more of a variety of channels, such as by telephone, email, or the like.

At 1220, the user determines a volume of drainage. This can involve calculating a volume based on the markings, type of nasal drip pad, and the like. The user determines, at 1230, whether the amount of drainage exceeds anticipated levels. The user determines, at 1240, whether the amount of drainage is so excessive that the person should seek medical attention. If the person should seek medical attention, as determined by the user at 1240, the user refers the person to a medical facility.

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims.

What is claimed is:

1. A nasal drip pad comprising:
   an absorber, wherein
      the absorber comprises absorbent material, and
      the absorber comprises an interior surface and an exterior surface;
   a positioner, wherein
      the positioner comprises one or more straps,
      a first end of the one or more straps is coupled to the absorber at a first point that is proximal to a first end of the absorber,
      a second end of the one or more straps is coupled to the absorber at a second point that is proximal to a second end of the absorber, and
      the positioner is configured to position the absorber below a nose of a user, such that
         a bottom edge of the interior surface is positioned against a face of the user below the nose of the user, such that the bottom edge maintains contact with the face of the user below the nose of the user, so as to form a seal between the bottom edge and the face of the user, and
         a top edge of the interior surface is positioned against the nose of the user, such that, when positioned, the absorber and the face of the user describe a volume therebetween,
         the volume is maintained by maintaining a shape of the absorber,
         the shape of the absorber is maintained by
            a first formable member located proximal to the top edge, and fastened between a first upper location proximal to the first end of the absorber and a second upper location proximal to the second end of the absorber, and a second formable member located proximal to the bottom edge, and fastened at a first lower location proximal to the first end of the absorber and a second lower location proximal to the second end of the absorber; and
an estimator, wherein
the estimator is coupled to the exterior surface of the absorber,
the positioner is configured to position the absorber and the estimator below the nose in a horizontal position, such that the absorber is positioned to receive drainage from the nose,
the estimator comprises a plurality of markings,
the plurality of markings are graduated in a vertical direction,
each of the plurality of markings indicates a corresponding estimated amount of a plurality of estimated amounts, and
each corresponding estimated amount of the plurality of estimated amounts represents an estimated amount of drainage from the nose of a plurality of estimated amounts of drainage from the nose into the volume.

2. The nasal drip pad of claim 1, further comprising:
a non-absorbent shield, wherein the non-absorbent shield is an exterior surface of the absorber, and the non-absorbent shield is configured to prevent spillage from the nasal drip pad.

3. The nasal drip pad of claim 1, wherein a thickness of the absorber is variable.

4. The nasal drip pad of claim 3, wherein the thickness of the absorber becomes progressively thicker towards an edge of the absorber.

5. The nasal drip pad of claim 1, further comprising:
an adjuster configured to adjust a length of the positioner.

6. The nasal drip pad of claim 1, wherein the absorber is detachably coupled to the positioner.

7. The nasal drip pad of claim 1, wherein the positioner comprises an adhesive at at least one of a first end and/or a second end, such that the first end and/or the second end is/are detachably coupled to the absorber.

8. The nasal drip pad of claim 1, wherein
the markings provide an estimate of an amount of fluid absorbed by the absorber,
wherein
the drainage comprises the fluid absorbed by the absorber,
a distance between each marking of the plurality of markings and a next marking of the plurality of markings corresponds to an absorbency of a portion of the absorbent material between the each marking and the next marking of the plurality of markings,
each marking of the markings corresponds to an estimator value of a plurality of estimator values, and
each of the plurality of estimator values corresponds to the absorbency of the portion of the absorbent material between the each marking and a previous marking of the plurality of markings.

9. The nasal drip pad of claim 8, wherein
the absorbent material increases in absorbency from the top edge to the bottom edge by
virtue of a thickness of the absorbent material becoming progressively thicker towards the bottom edge.

10. The nasal drip pad of claim 8, wherein
the portion is one of a plurality of portions,
a thickness of the absorber in each portion of the plurality of portions is described by a thickness value,
the estimator describes an area of a surface of the each portion,
an absorbency of the each portion is described by an absorbency coefficient,
an estimate of an amount of fluid absorbed by the each portion is the area of the each portion multiplied by the thickness value of the each portion multiplied by the absorbency of the each portion, and
the estimate of the amount of fluid absorbed by the absorber is a sum of the estimate of the amount of fluid absorbed by the each portion, for each of one or more portions of the plurality of portions that have absorbed the fluid.

11. The nasal drip pad of claim 10, wherein
the estimated amount of drainage is also based, at least in part, on the amount of fluid absorbed by the absorber.

12. The nasal drip pad of claim 11, wherein
a rate of fluid loss is determined by dividing the estimate of the amount of fluid absorbed by the absorber by a time value.

13. The nasal drip pad of claim 12, wherein
a current estimated amount of drainage is determined based, at least in part, on the rate of fluid loss and the time value,
the current estimated amount of drainage in one of the plurality of estimated amounts of drainage, and the time value is an amount of time the nasal drip pad has been worn by the user.

14. The nasal drip pad of claim 1, wherein
a variable amount of material is included in the absorber, which results in the absorber having a variable thickness, and
a spacing between one of the plurality of markings and a next one of the plurality of markings varies according to the variable thickness.

15. The nasal drip pad of claim 1, wherein the absorber further comprises:
a plurality of layers of absorbent material.

16. The nasal drip pad of claim 15, wherein
a spacing between one of the plurality of markings and a next one of the plurality of markings varies according to an absorption capacity of each of the plurality of layers.

17. The nasal drip pad of claim 16, wherein each layer of the plurality of layers is independently attached to a next layer of the plurality of layers using an adhesive.

18. The nasal drip pad of claim 17, wherein a surface of a layer of the plurality of layers in contact with a user's skin is coated with a non-stick coating.

19. The nasal drip pad of claim 18, wherein
the positioner is configured to cause the surface of the layer of the plurality of layers in contact with the user's skin to form a seal with the user's skin.

20. The nasal drip pad of claim 1, wherein
the estimator is vertically divided into a plurality of horizontal regions by the markings,
each horizontal region of the plurality of horizontal regions is defined by a marking of the plurality of markings and a next marking of the plurality of markings,
the marking is at a vertically lower position on the estimator than a vertical position of the next marking,
each horizontal region of the plurality of horizontal regions is designated by a color of the each horizontal region, and a vertically lowest horizontal region of the plurality of regions is shaded green to indicate a safe level of drainage.

21. The nasal drip pad of claim 20, wherein another horizontal region of the plurality of horizontal regions is shaded with a color that indicates an unsafe level of drainage, and
the another horizontal region is at a vertically higher position on the estimator than a vertical position of the vertically lowest horizontal region.

22. The nasal drip pad of claim 1, wherein
the one or more straps are configured to be placed around a head of the user such that the shape of the absorber is maintained by a positioning of each of the one or more straps around the head of the user.

23. The nasal drip pad of claim 1, wherein
the first point is proximal to a top-right area of the absorber,
the second point that is proximal to a top-left area of the absorber,
the positioner is further coupled to the absorber at a third point that is proximal to a bottom-right area of the absorber, and a fourth point that is proximal to a bottom-left area of the absorber, and
the shape of the absorber is further maintained by the first formable member being attached between the first point and the second point, and
the second formable member being attached between the third point and the fourth point.

24. The nasal drip pad of claim 1, wherein
the one or more straps comprise a plurality of straps
the plurality of straps comprise a first strap and a second strap, wherein
each of the first strap and the second strap are configured to be placed around a head of the user, and
the first strap is attached at a first end of the first strap to a first end of the first formable member and at a second end of the first strap to a second end of the first formable member, and
the second strap is attached at a first end of the second strap to a first end of the second formable member and at a second end of the second strap to a second end of the second formable member, and
the first strap and the second strap are configured to be positioned such that the shape of the absorber is maintained by a position of the first strap and a position of the second strap.

* * * * *